United States Patent [19]

Hudek et al.

[11] 4,231,374

[45] Nov. 4, 1980

[54] PROCEDURE AND DEVICE FOR THE DETECTION OF EXTRAORDINARY EVENTS IN A SERIES OF ESSENTIALLY PERIODICALLY RECURRING NORMAL EVENTS

[75] Inventors: Karl Hudek, Erlangen; Kurt Weigert, Nuremberg, both of Fed. Rep. of Germany

[73] Assignee: Siemens Aktiengesellschaft, Berlin & Munich, Fed. Rep. of Germany

[21] Appl. No.: 953,896

[22] Filed: Oct. 23, 1978

[30] Foreign Application Priority Data

Nov. 7, 1977 [DE] Fed. Rep. of Germany ....... 2749791

[51] Int. Cl.³ .............................................. A61B 5/04
[52] U.S. Cl. .................................................. 128/702
[58] Field of Search ................. 128/702, 703, 706, 707

[56] References Cited

U.S. PATENT DOCUMENTS

| | | | |
|---|---|---|---|
| 3,608,545 | 9/1971 | Novack et al. | 128/706 |
| 3,968,431 | 7/1976 | Ekstrom | 128/706 |
| 4,066,069 | 1/1978 | Dolch | 128/706 |

*Primary Examiner*—William E. Kamm

*Attorney, Agent, or Firm*—Hill, Van Santen, Steadman, Chiara & Simpson

[57] ABSTRACT

In an illustrative embodiment EKG normal pulses have a time separation representing a monitoring interval, and upon the occurrence of a normal event (normal pulse), circuitry is activated to determine whether further events occur during the monitoring interval. The monitoring interval can be set at a constant value or a variably concomitant value as a function of the interval between the periodic normal events. Upon switching over from constant value to concomitant value of the monitoring interval, a comparator is activated, which comparator compares a time interval value between periodic normal events determined by means of a frequency-voltage converter with the constant value of the monitoring interval. A regulating element controls the converter output voltage by means of amplification alteration in such manner that it is altered toward the direction of the constant value of monitoring interval. Upon equality, the comparator generates a shutdown signal. The voltage value of the frequency-voltage converter serves then, after shutdown of the regulation upon attainment of the now-constant amplification factor, for the concomitant setting of the monitoring interval. Thus, the setting follows largely automatically, so that the correct value sets itself.

12 Claims, 1 Drawing Figure

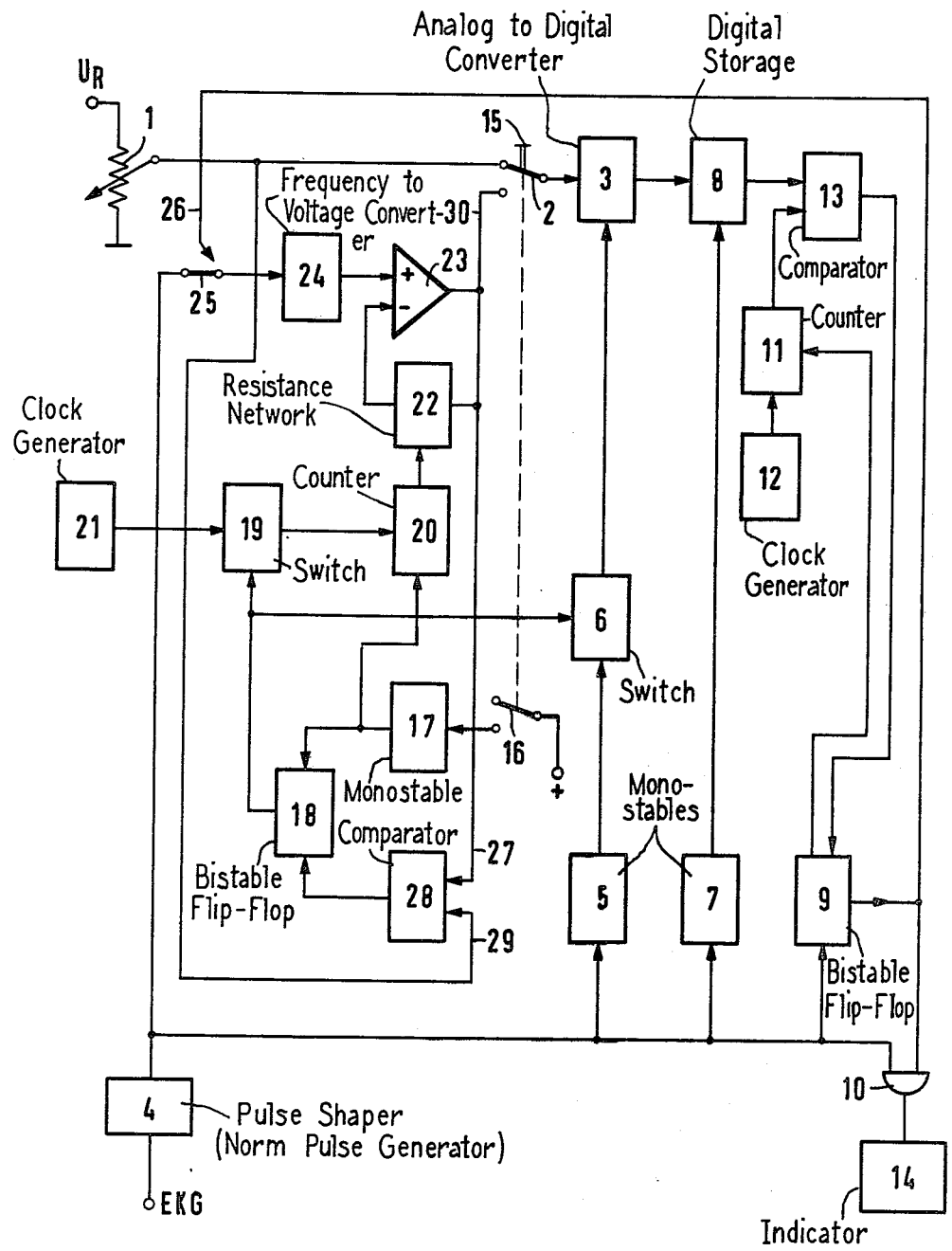

PROCEDURE AND DEVICE FOR THE DETECTION OF EXTRAORDINARY EVENTS IN A SERIES OF ESSENTIALLY PERIODICALLY RECURRING NORMAL EVENTS

BACKGROUND OF THE INVENTION

The invention relates to a procedure and to a device for the detection of extraordinary events in a series of essentially periodically recurring normal events, particularly extra systoles in the EKG, whereby upon each occurrence of a normal event a monitoring interval starts and is examined to determine whether further events, which are evaluated as extraordinary, occur with this monitoring interval; and whereby the monitoring interval can be optionally set at a constant value or at a value that is variable concomitant dependent upon the time interval between specific normal events that succeed one another periodically.

When switching over from a constant value to the variably concomitant value of the monitoring interval there arises the exigency that after each switching-over operation the concomitant monitoring interval must be set anew in percentages of the momentary interval of normal events (for example R-tooth intervals in the EKG). This operation is time-consuming and troublesome, as long as it must be undertaken manually.

SUMMARY OF THE INVENTION

The object of the present invention is to automate the adjustment to the point that, after switching over from the fixed monitoring interval to the concomitant interval, the correct value always sets itself. The object is inventively achieved in that, upon switching over from a constant value to the variably concomitant value of the monitoring time interval, a comparator is activated, which compares a time interval value between the periodic normal events determined by means of a frequency-voltage converter with the previously set constant value of the monitoring interval and which comparator controls a control element for the output voltage of the frequency-voltage converter for the purpose of altering the output voltage in the direction of the constant value of the monitoring interval by means of amplification factor alteration, and whereby a shutdown signal is generated by means of the comparator for further regulation by means of the voltage control element as soon as the voltage values for constant value of the monitoring interval and time interval value between normal events are equal; and in that upon the shut down of the voltage control element at a now constant amplification factor the output voltage of the frequency-voltage converter amplified with this constant value is the voltage value for the concomitant setting of the monitoring time interval.

The apparatus for the implementation of this inventive procedure, which thus makes the automatic adjustment of the concomitant monitoring interval after switching over from fixed to variable operation, is characterized by a comparator for the time interval value between periodic normal events determined by means of the frequency-voltage converter and the constant value of the monitoring interval adjusted by means of an adjustment element; as well as by a voltage control element for the control of the output voltage of the frequency-voltage converter with a shutdown installation for the shutting-down as a function of the output signal of the comparator.

Further advantages and details of the invention derive from the following description of a sample embodiment on the basis of the drawing in conjunction with the subclaims; and other objects, features and advantages will be apparent from this detailed disclosure and from the appended claims.

BRIEF DESCRIPTION OF THE DRAWING

The single FIGURE shows a sample embodiment specifically for the detection of extra systoles of an EKG by means of a basic circuit diagram.

DETAILED DESCRIPTION

In the basic circuit diagram according to the FIGURE, the adjustment of a constant value of the monitoring time by means of voltage divider 1 during visual observation of the actual electrocardiogram (for example at an oscilloscopic tube not illustrated) ensues first. The manually adjusted dividing value for supply voltage $U_R$, which corresponds to the constant value of the monitoring interval, is transmitted via a switch 2 to an analog-digital converter 3. The conversion of the analog voltage value into a digital value ensues as a function of standard (or norm) pulses from the EKG which are generated by means of a pulse shaping stage 4 (R-tooth discriminator) always with the occurrence of a QRS complex. Each of these standard (or norm) pulses sets, with its initial edge, a monostable flip-flop 5 that triggers the conversion process in the analog-digital converter 3 via a switch 6, which is closed in this state. The end edge of each norm pulse triggers a second monostable flip-flop 7 which activates a digital storage 8 to fetch and to store the signal information from the analog-digital converter 3. Each norm pulse of the norm pulse generator 4, however, also simultaneously activates a bistable flip-flop 9 and goes, moreover, to the one comparison input of an AND element 10. Upon each occurrence of the norm pulse, the bistable flip-flop 9 activates a counter 11 to the effect that it is back-shaped to zero and subsequently released for the enumeration of clock pulses of a clock generator 12. The counter reading of the counter 11 is compared with the digital information of the storage 8 in a comparator 13. When there is equality between the two data, then the comparator 13, on its output side, returns the bistable flip-flop 9 to its starting condition. The duration of the activation of the bistable flip-flop 9 then corresponds to the respective value of the monitoring interval delivered by the analog-digital converter 3. An output pulse of the bistable flip-flop developed during the duration of the activation lies at the other comparison input of the AND element 10. Accordingly, the AND element is only penetrable to norm pulses of the EKG norm pulse generator 4 when these fall in the setting time of the bistable flip-flop 9, i.e. in the monitoring interval. Since normal QRS complexes of the EKG follow one another at time intervals that are always greater than the monitoring interval, it can only be a question of extra systoles in the case of QRS complexes let through by the AND element 10 and indicated or registered, respectively, by an indicator 14. The device 14 therefore indicates the presence of extra systoles.

The detection and indication of extra systoles ensues in the manner described in the case of a constant value as well as in the case of the variable concomitant value of the monitoring interval. The switching-over from a constant value of the monitoring interval to variable concomitant value ensues in a simple manner by means of the actuation of a key 15. The actuation of key 15 effects the switching-over of switch 2 as well as of a second switch 16 coupled with it into the other switching position. The switching-over of switch 16 effects that a monostable flip-flop 17 is joined to positive potential and thereby thrust into the unstable condition. The output pulse generator by the monostable flip-flop 17 sets, on the one hand, a bistable flip-flop 18 which closes a switch 19 with its output. Moreover, the switch 6 in the line between the monostable flip-flop 5 and the analog-digital converter 3 is opened. But the output pulse of the monostable flip-flop 17, on the other hand, also sets a counter 20 to zero; clock pulses of a clock generator 21 (free running) are thus counted up in the counter 20 when switch 19 is closed. The counter 20 is a binary counter, which connects the resistors with graded resistance values of a negative feedback network 22 of a voltage amplifier 23 (operational amplifier), to one another according to the binary count value to the end that the output voltage rises in successive step-shaped increments at the output of the voltage amplifier 23 as successive count values are registered by counter 20. The input voltage of the voltage amplifier 23 is a voltage of a heart frequency-voltage converter 24 inversely proportional to the mean heart frequency. Accordingly, the heart frequency-voltage converter 24 receives at its input side the output norm pulses of the EKG norm pulse transducer 4. A switch 25 is interposed in the feed path of these impulses to the heart frequency-voltage converter 24, which switch 25 is open via the control line 26 during the interval in which the bistable flip-flop 9 is activated, i.e. during the monitoring interval. Only upon completion of the monitoring interval, i.e. upon the resetting of the flip-flop 9, is the switch 5 brought into the closed position illustrated. In this manner, impulses that develop during the monitoring time, i.e. particularly extra systoles, are prevented from reaching the heart frequency-voltage converter 24; hereby, an influence of extra systoles on the mean heart frequency value of the heart frequency-voltage converter 25 is thwarted.

In the basic circuit diagram of the FIGURE, therefore, the amplification for the voltage delivered from the heart frequency-voltage converter 24 and inversely proportional to the mean heart frequency is increased step-by-step from the outputs of the counter 20, by means of the corresponding control of the negative feedback network 22. The voltage rising step-by-step at the output of the voltage amplifier 23 is now conducted via a signal line 27 to the one input of a comparator 28. The other input of the comparator 28 lies at the constant value of the monitoring interval (i.e. the output voltage of the voltage divider 1) via the signal line 29. The comparator compares the two voltages with one another. As soon as the step voltage of the voltage amplifier 23 reaches the constant value of the monitoring interval, i.e. upon voltage equality at the inputs of the comparator, the comparator 28 switches over and sets the bistable flip-flop 18 back into the initial state. Thereby the switch 19 is opened and the counting-in process of pulses into the counter 20 is interrupted. The amplification factor of the amplifier 23 is held constant corresponding to the attained count of the counter 20 via the negative feedback network 22. Every change in the mean heart frequency now effects a voltage signal fluctuating in magnitude at the output of the voltage amplifier 23 via the heart frequency-voltage converter 24 as well as via the amplifier 23 which is now set to provide a constant amplification degree. When the heart frequency rises, then the output voltage of the amplifier 23 falls correspondingly below the output voltage of the divider 1. When, on the other hand, the heart frequency falls, then the output voltage of the voltage amplifier 23 rises bove this output value of divider 1. The voltage fluctuations are communicated via the signal line 30 to the analog-digital converter 3 which, upon any given occurrence of a norm pulse of the EKG norm pulse transducer 4, converts them with switch 6 now being again closed by means of the setting of the monostable flip-flop 5. The respectively developing digital voltage signal then effects a time interval via the already described processing circuits 7 through 13 which interval is the variable concomitant monitoring interval as a function of fluctuations of the heart frequency.

The described apparatus thus allows, in the simplest manner, switching over from a fixed constant value to a variably concomitant value of the monitoring interval, whereby, upon switching over, the variably concomitant value is always correctly set by itself, i.e. automatically.

It will be apparent that many modifications and variations may be effected without departing from the scope of the novel concepts and teachings of the present invention.

We claim as our invention:

1. Procedure for the detection of extraordinary events in a series of essentially periodically recurring normal events, particularly extra systoles in the EKG, said procedure comprising:

manually setting a control (1) to a selected fixed value representing a time period corresponding to a fixed monitoring interval between successive occurrences of a normal event, in a first mode of operation responding to each occurrence of the normal event to begin scanning for a further event, and continuing such scanning for a fixed time duration which corresponds to said selected fixed value, and so monitoring for a further event after each normal event directly according to said selected fixed value so long as the first mode of operation continues, shifting over from said first mode of operation to a second mode of operation, and during said second mode of operation:

(a) activating a comparator circuit (17, 18, 28) with the compartor having a first input (29) receiving a signal in accordance with said selected fixed value from the control (1) and having a second input (27) connected with a voltage regulator (22, 23), (b) monitoring the actual repetition rate of currently occurring normal events by means of a frequency to voltage converter (24), (c) supplying the output of the frequency to voltage converter (24) to said voltage regulator (22, 23) with the output of the voltage regulator being connected to the second input (27) of he comparator circuit (17, 18, 28), (d) step by step adjusting the amplification factor of the voltage regulator (22, 23) until the output therefrom as supplied to the second input (27) of the comparator circuit matches the signal at the first input (29) thereof, (e) responding to the matching at the first and second inputs of the comparator circuit (17, 18, 28) to fix the amplification factor at the currently adjusted value, and (f) thereafter during said second mode of operation supplying the output of the voltage regulator (22, 23) with the amplification factor thereof adjusted according to steps (d) and (e) as a control value representing the time duration of a concomitantly variable monitoring interval, and thereafter responding to each occurrence of the normal event to begin scanning for an extraordinary event, and continuing such scanning for a time duration which is a function of said control value during said second mode of operation.

2. Apparatus for the implementation of the procedure according to claim 14, comprising manually adjustable control means (1) for selecting a selected fixed value representing a time period corresponding to a fixed monitoring interval between successive occurrences of a normal event, switchover means (2) for selecting between a first mode of operation and a second mode of operation, monitoring means (3, 5-13) connected with said manually adjustable control means (1) under the control of said switchover means (2) and operable in the first mode of operation as selected by said switchover means (2) to respond to each occurrence of the normal event to begin scanning for a further event, and continuing such scanning for a fixed time duration which corresponds to said selected fixed value, and so monitoring for a further event after each normal event directly according to said selected fixed value so long as the first mode of operation continues, comparator circuit means (17, 18, 28) comprising a comparator (28) having a first input (29) connected with said control means (1) for receiving a signal in accordance with said selected fixed value, and having a second input (27), voltage regulator means (22, 23) having a frequency to voltage converter (24) for supplying a signal to said regulator means (22, 23) in accordance with the frequency of occurrence of normal events, having step by step amplification adjusting means (19-21) connected therewith for controlling the amplification factor thereof, and having an output connected to the second input (27) of said comparator (28), and also connected under the control of said switchover means with said monitoring means (3, 5-9, 11-13) so that in said second mode of operation as selected by said switchover means (2) the output of said regulator means (22, 23) is supplied to said monitoring means, said comparator circuit means (17, 18, 28) being responsive to switchover of said switchover means (2) to said second mode of operation to activate said step by step amplification adjusting means (19-21) to progressively change the amplification factor of the regulator means (22, 23) until said comparator (28) signals a match between its first and second inputs, said monitoring means (3, 5-9, 11-13) thereafter during said second mode of operation responding to each occurrence of the normal event to begin scanning for an extraordinary event, and being responsive to the output of said regulator means (22, 23) to continue such scanning for a time duration which is a function of the output of said frequency to voltage converter (24) and the amplification factor of said regulator means as set by said step by step amplification adjustment means (19-21), thereby to provide a concomitantly variable monitoring interval.

3. Apparatus according to claim 2, with the voltage regulator means comprising a voltage amplifier (23), and a negative feedback network (22) connected between the output and the input of said voltage amplifier (23), and said step by step amplification adjusting means being operable for changing the value of the resistance of said feedback network (22) during said second mode of operation in successive steps such that the amplification factor of the voltage amplifier (23) changes step by step and generates an output voltage that rises in a step form.

4. Apparatus according to claim 3 with said step by step amplification adjusting means comprising a binary counter (20) controlling said negative feedback network (22), said negative feedback network (22) comprising a series of resistors which are connected to one another in accordance with the count of said binary counter (20).

5. Apparatus according to claim 4 with said comparator circuit means comprising a monostable flip-flip (17) connected with said binary counter (20) and responsive to switchover to said second mode of operation to set and binary counter (20) to a count initiation value.

6. Apparatus according to claim 3 with said step by step amplification adjusting means comprising a counter (20) controlling the value of the resistance of said resistance network (22) in accordance with the count thereof, and a clock generator (21) for connection with said counter (20), and a switching element (19) controlling connection of said clock generator (21) with said counter (22), said comparator circuit means comprising a bistable flip-flop (18) controlling said switching element (19), and a monostable flip-flop (17) connected with said bistable flip-flop (18) and responsive to selection of said second mode of operation by said switchover means (2) to set said bistable flip-flop to an active state and thereby to actuate said switching element (19) to initiate a step by step amplification adjustment cycle.

7. Apparatus according to claim 6 with said comparator (28) being connected with said bistable flip-flop (18) for resetting the bistable flip-flop (18) out of its active state when a match is attained between the first and second inputs of said comparator to stop the counting of said counter so that the resistance value of said negative feedback network (22) is held constant and thereby the amplification factor of the voltage regulator means is held constant corresponding to the attained count of said counter (20).

8. Apparatus according to claim 2 with said monitoring means comprising a setting mechanism (3, 5, 7-13) connected with said control means (1) in said first mode of operation, and connected with said voltage regulator means (22, 23) in said second mode of operation, and being responsive to the fixed value selected by said control means (1) to set the time period of the fixed monitoring interval in accordance therewith in said first mode of operation, an interlock switch (6) responsive to an interlock signal for controlling said setting means for preventing change of said time period thereby, said comparator circuit means (17, 18, 28) being connected with said interlock switch (6) and being operable to supply said interlock signal thereto during the activation of the step by step amplification adjusting means (19-21) to suppress operation of the setting mechanism (3, 5, 7-13).

9. Apparatus according to claim 8 with said comparator circuit means (17, 18, 28) being responsive to a match at the first and second inputs of said comparator (28) to interrupt supply of said interlock signal to said interlock switch (6), thereby to place said setting mechanism (3, 5, 7–13) in operation for setting of the duration of the scanning for a further event in accordance with the output from said voltage regulator means (22, 23).

10. Apparatus according to claim 8 with said comparator circuit means comprising a monostable flip-flop (17) responsive to switchover to said second mode of operation to supply an output signal,
   a bistable flip-flop (18) connected with said interlock switch (6) and responsive to the output signal from said monostable flip-flop (17) to supply said interlock signal to said interlock switch (6),
   said bistable flip-flop (18) being connected with the comparator (28) and being responsive to a match at the first and second inputs thereof to interrupt said interlock signal.

11. Apparatus according to claim 2 with said frequency to voltage converter (24) having an interlock switch (25) controlling the input thereto, and said monitoring means (3, 5–13) being connected with said interlock switch (25) for actuating said switch to suppress admission of pulse events to said frequency to voltage converter (24) for the duration of a concomitantly variable monitoring interval.

12. Apparatus according to claim 2, with said monitoring means comprising an analog-digital converter (3) selectively connectable with said control means (1) and with said voltage regulator means (22, 23) as selected by said switchover means (2), comparison means (13) having a first input for connection with said analog-digital converter (3) for receiving a digitalized voltage value in accordance with the output of said analog-digital converter (3) and having a second input, and a counter unit (11, 12) connected with said second input of said comparison means (13) and operable in conjunction with said comparison means (13) for establishing a time interval proportional to the digitalized voltage value at the first input of said comparison means (13), thereby to define the time duration of a concomitantly variable monitoring interval.

* * * * *